(12) United States Patent
Sugano et al.

(10) Patent No.: US 7,528,220 B2
(45) Date of Patent: May 5, 2009

(54) CYANATE ESTER COMPOUND, FLAME-RETARDANT RESIN COMPOSITION, AND CURED PRODUCT THEREOF

(75) Inventors: Yuuichi Sugano, Niigata (JP); Masayuki Katagiri, Niigata (JP); Daisuke Ohno, Tokyo (JP); Seiji Kita, Kurashiki (JP); Masanobu Sogame, Tokyo (JP); Hironao Fukuoka, Tokyo (JP); Masayoshi Ueno, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 306 days.

(21) Appl. No.: 11/270,661

(22) Filed: Nov. 10, 2005

(65) Prior Publication Data

US 2006/0084787 A1    Apr. 20, 2006

Related U.S. Application Data

(63) Continuation-in-part of application No. 11/057,182, filed on Feb. 15, 2005, now abandoned.

(30) Foreign Application Priority Data

Feb. 18, 2004    (JP) ............... 2004-041055

(51) Int. Cl.
| | |
|---|---|
| C08G 73/10 | (2006.01) |
| C08G 73/16 | (2006.01) |
| C07C 265/12 | (2006.01) |
| C08K 5/205 | (2006.01) |
| C08K 5/29 | (2006.01) |
| C09D 5/18 | (2006.01) |

(52) U.S. Cl. ............... 528/422; 528/407; 528/322; 525/423; 524/563; 428/463; 560/359

(58) Field of Classification Search ............... 528/422, 528/407, 322; 525/423; 560/359; 524/563; 428/463

See application file for complete search history.

(56) References Cited

U.S. PATENT DOCUMENTS

2002/0055648 A1    5/2002 Lin et al.

FOREIGN PATENT DOCUMENTS

| EP | 0 326 806 A2 | 8/1989 |
|---|---|---|
| EP | 0 581 268 A1 | 2/1994 |

*Primary Examiner*—Duc Truong
(74) *Attorney, Agent, or Firm*—Wenderoth, Lind & Ponack, L.L.P.

(57) ABSTRACT

A cyanate ester compound represented by the formula (1),

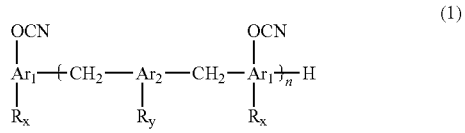

wherein $Ar_2$ represents a phenylene group, a naphthylene group or a biphenylene group, $Ar_1$ represents a naphthylene group or a biphenylene group when $Ar_2$ is a phenylene group, or $Ar_1$ represents a phenylene group, a naphthylene group or a biphenylene group when $Ar_2$ is a naphthylene group or a biphenylene group, $R_x$ represents all substituents of $Ar_1$, each $R_x$ is the same or different and represents hydrogen, an alkyl group or an aryl group, Ry represents all substituents of $Ar_2$, each $R_y$ is the same or different and represents hydrogen, an alkyl group or an aryl group, and n is an integer of 1 to 50.

17 Claims, No Drawings

CYANATE ESTER COMPOUND, FLAME-RETARDANT RESIN COMPOSITION, AND CURED PRODUCT THEREOF

This application is a continuation-in-part of now abandoned application Ser. No. 11/057,182, filed Feb. 15, 2005 now ABN.

FIELD OF THE INVENTION

The present invention relates to a novel cyanate ester compound, a thermosetting resin composition containing the above compound and a cured product thereof. The cyanate ester compound of the present invention can provide a polymer material excellent in flame resistance, heat resistance and low dielectric characteristics by polymerizing the cyanate ester compound itself or copolymerizing the cyanate ester compound with another resin. Such a thermosetting resin composition can be widely used for applications such as an electrical insulating material, a resin for a resist, a semiconductor-sealing resin, an adhesive for a printed wiring board, a matrix resin for a laminate or a prepreg used for electrical devices, a buildup laminate material, a resin for a fiber-reinforced plastic, a sealing resin for a liquid crystal display panel, a resin for a color filter of liquid crystal, a coating composition, various coating agents and an adhesive.

PRIOR ARTS OF THE INVENTION

Cyanate ester resins generate a triazine ring by curing and have been widely used as raw materials for a variety of functional polymer materials such as structural composite materials, adhesives, electrical insulating materials or electrical and electric parts due to their high heat resistance and excellent electric characteristics. However, in recent years, as higher performances are required in their application fields, physical properties required as a functional polymer material become severer increasingly. As such physical properties, for example, there are required flame resistance, heat resistance, low dielectric constant, low dielectric loss tangent, weather resistance, chemical resistance, low moisture absorptivity, high fracture toughness, etc. So far, these required properties have not completely satisfied.

In a printed wiring board material field, for example, as a communication frequency and a clock frequency are increasing, a material having a low dielectric constant and a low dielectric loss tangent becomes required. For this reason, cyanate resins excellent in dielectric characteristics come to be used. In this case, it is necessary to impart flame resistance in view of safety from fire and bromine compounds having high flame resistance are used. For example, brominated bisphenol A (JP-B-4-24370), a glycidyl ether of brominated phenol novolak (JP-A-2-286723), brominated maleimides (JP-A-7-207022), halogen-containing monofunctional cyanates (JP-A-6-122763) and an additive type bromine compound having no reactivity with a cyanate ester compound (JP-A-2000-95938) are known.

Such bromine compounds have high flame resistance, while corrosive bromine and hydrogen bromide are separated there from by thermal decomposition. Therefore, materials which do not contain a bromine type flame retardant are desired.

Then, phosphorus-containing compounds, nitrogen-containing compounds and sulfur-containing compounds have been studied as a flame retardant instead of bromine. For example, triphenyl phosphate, resorcinol bis(diphenylphosphate), etc., are studied as a phosphorus compound which is often incorporated into an epoxy resin. However, when such a compound is incorporated in a large amount, heat resistance, moisture resistance, water absorptivity, etc., decrease in many cases.

For overcoming the above problem, a method in which a phosphorus compound having a phenolic hydroxyl group is added to a cyanate compound (for example, JP-A-2003-128928, JP-A-2003-128753 and JP-A-2003-128784) is known. However, the phosphorus compounds also have a toxic problem. Furthermore, melamine, guanidine, etc., are used as a nitrogen compound. However, the nitrogen compound is insufficient in flame resistance when it is used alone.

On the other hand, metal hydroxides such as aluminum hydroxide and magnesium hydroxide are known as a flame retardant.

However, there is apprehension that the incorporation of the metal hydroxide causes a decrease in dielectric characteristics, heat resistance, impact resistance or moldability. Further, when an inorganic filler such as a spherical fused silica is used in a large amount for decreasing a combustible component and securing flame retardancy, as is used for an epoxy resin, the melt viscosity of a molding material rises, a deterioration in moldability occurs, a decrease in adhesive strength occurs because of a decrease in wettability to a base material, or a deterioration in dielectric characteristics occurs, in some cases.

Further, antimony type flame retardants such as antimony trioxide, which are widely used in combination with a brominated epoxy resin, have a problem such as an apprehension of chronic toxicity since they are toxic substances. From the above viewpoints, thermosetting resins themselves are desired to have higher flame retardancy than ever.

Moreover, a lot of attempts have been made for improving heat resistance, low dielectric constant, low dielectric loss tangent, weather resistance, chemical resistance, low absorption, high fracture resistance, moldability, adhesion, etc., in addition to flame retardancy. For example, JP-A-6-228308 discloses a method for producing 5 a cured product excellent in thermal stability by combining a monocyanate with a dicyanate and JP-A-6-49238 discloses a method which aims at a low dielectric constant and a low dielectric loss tangent by combining a monofunctional cyanate ester compound with a polyfunctional cyanate ester compound.

Further, JP-A-6-122763 discloses a method for producing a low-absorptive, flame-retardant cyanate ester curable resin composition by incorporating a halogen-containing monofunctional cyanate ester in order to achieve a low dielectric constant and a low dielectric loss tangent. JP-A-6-122763 have a description about the cyanate ester in a wide range. However, an aromatic monofunctional cyanate ester having bromine as a functional group is essential for the maintenance of flame retardancy, so that JP-A-6-122763 does not succeeds in improving the flame retardancy with the cyanate ester resin alone.

Further, Japanese Kohyo No. 2002-531989 provides an aromatic cyanate ester compound containing at least two rings each of which is bonded with a group containing an unsaturated group. JP-A-63-250359 provides a fluorine-containing dicyanate ester. JP-A-2002-206048 provides a method for attaining flame retardancy by using a phenol novolak type cyanate ester. However, none of them teach a cured product formed of a cyanate ester compound alone which product practically has all of low dielectric characteristics, flame retardancy and heat resistance.

SUMMARY OF THE INVENTION

It is an object of the present invention to provide a novel cyanate ester compound capable of giving a cured product not only having excellent flame retardancy but also having a low dielectric constant, a low dielectric loss tangent and high heat resistance, a curable resin composition containing the above compound and a cured product obtained by curing the above resin composition.

The present inventors have made diligent studies and as a result found that a cyanate ester compound represented by the formula (1), preferably compounds represented by the formulae (2)-(4), more preferably compounds represented by the formulae (5)-(7), gives a cured product which is excellent in flame resistance and has a low dielectric constant, a low dielectric loss tangent and high heat resistance. Accordingly, the present inventors have completed the present invention.

The present invention provides a cyanate ester compound represented by the formula (1), preferably a cyanate ester compound represented by any one of the formulae (2) to (4), more preferably a compound represented by any one of the formulae (5) to (7),

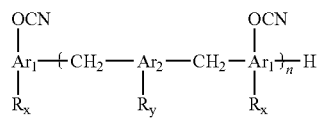
(1)

wherein $Ar_2$ represents a phenylene group, a naphthylene group or a biphenylene group, $Ar_1$ represents a naphthylene group or a biphenylene group when $Ar_2$ is a phenylene group, or $Ar_1$ represents a phenylene group, a naphthylene group or a biphenylene group when $Ar_2$ is a naphthylene group or a biphenylene group, $R_x$ represents all substituents of $Ar_1$, each $R_x$ is the same or different and represents hydrogen, an alkyl group or an aryl group, $R_y$ represents all substituents of $Ar_2$, each $R_y$ is the same or different and represents hydrogen, an alkyl group or an aryl group, and n is an integer of 1 to 50,

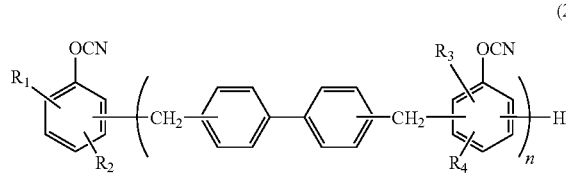
(2)

wherein $R_1$ to $R_4$ are the same or different and represent hydrogen or an alkyl group, n is an integer of 1 to 50, and the position of each substituent of aromatic rings can be arbitrarily selected,

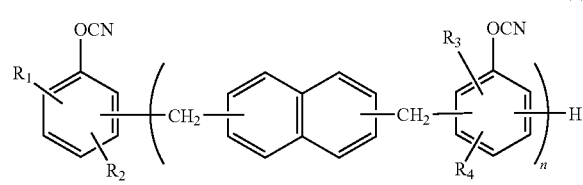
(3)

wherein $R_1$ to $R_4$ are the same or different and represent hydrogen or an alkyl group, n is an integer of 1 to 50, and the position of each substituent of aromatic rings can be arbitrarily selected,

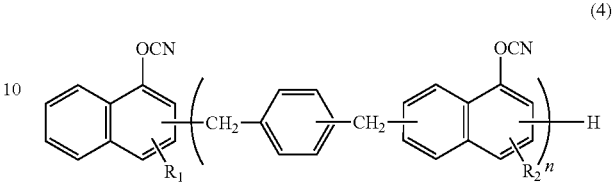
(4)

wherein $R_1$ and $R_2$ are the same or different and represent hydrogen or an alkyl group, n is an integer of 1 to 50, and the position of each substituent of aromatic rings can be arbitrarily selected,

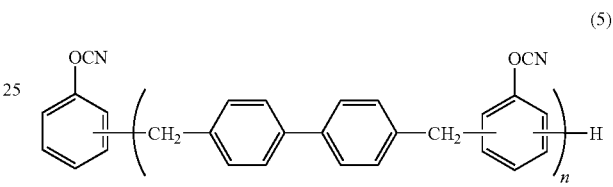
(5)

wherein n is an integer of 1 to 50,

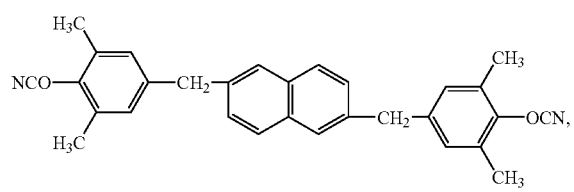
(6)

and

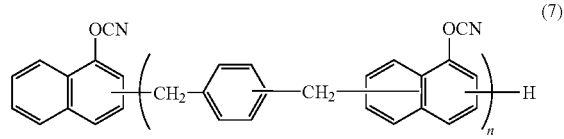
(7)

wherein n is an integer of 1 to 50.

The present invention further provides a curable resin composition containing the above cyanate ester compound represented by the formula (1), preferably a curable resin composition containing the cyanate ester compound represented by any one of the formulae (2) to (4), more preferably a curable resin composition containing the cyanate ester compound represented by any one of the formulae (5) to (7), and a cured product obtained by curing the above resin composition.

The present invention further provides a resin composition containing a cyanate ester compound of the formula (1) and an epoxy resin and preferably optionally containing an inorganic filler. The present invention further preferably provides a resin composition containing a cyanate ester compound of the formula (4) or the formula (7) and an epoxy resin. The present invention further provides a prepreg comprising the above resin composition and a base material, and a laminate or a metal-foil-clad laminate obtained by curing the above prepreg.

The present invention further provides a resin composition containing a cyanate ester compound of the formula (1) and a maleimide compound. The present invention further preferably provides a resin composition containing a cyanate ester compound of the formula (4) or the formula (7) and a maleimide compound. The present invention further provides a cured product obtained by curing the above resin composition.

EFFECT OF THE INVENTION

The cyanate ester of the present invention is capable of giving a cured product excellent in flame retardancy and has a low dielectric constant, a low dielectric loss tangent and a high glass transition temperature. For this reason, it is remarkably useful as a high function polymer material and can be used as a thermally and electrically excellent material for wide applications such as an electrical insulating material, an adhesive, a laminating material, a resist and a buildup laminate material.

DETAILED DESCRIPTION OF THE INVENTION

The present invention will be explained in detail hereinafter. In the cyanate ester compound represented by the formula (1), $Ar_2$ represents a phenylene group, a naphthylene group or a biphenylene group, and $Ar_1$ represents a naphthylene group or a biphenylene group when $Ar_2$ is a phenylene group or $Ar_1$ represents a phenylene group, a naphthylene group or a biphenylene group when $Ar_2$ is a naphthylene group or a biphenylene group. Specific examples of $Ar_1$ and $Ar_2$ include 1,4-phenylene group, 1,3-phenylene group, 4,4'-biphenylene group, 2,4'-biphenylene group, 2,2'-biphenylene group, 2,3'-biphenylene group, 3,3'-biphenylene group, 3,4'-biphenylene group, 2,6-naphthylene group, 1 5-naphthylene group, 1,6-naphthylene group, 1,8-naphthylene group, 1,3-naphthylene group and 1,4-naphthylene group.

In the cyanate ester compound represented by the formula (1), $R_x$ represents all substituents of $Ar_1$ and each $R_x$ is the same or different and represents hydrogen, an alkyl group or an aryl group. Specific examples of $R_x$ include a methyl group, an ethyl group, an isopropyl group, a n-butyl group, an i-butyl group, a tert-butyl group and an isomer pentyl group as the alkyl group and a phenyl group, an alkyl phenyl group, a naphthyl group, an alkyl naphthyl group, a biphenyl group and an alkyl biphenyl group as the aryl group.

In the cyanate ester compound represented by the formula (1), $R_y$ represents all substituents of $Ar_2$ and each $R_y$ is the same or different and represents hydrogen, an alkyl group or an aryl group. Specific examples of $R_y$ include a methyl group, an ethyl group, an isopropyl group, an n-butyl group, an i-butyl group, a tert-butyl group and an isomer pentyl group as the alkyl group and a phenyl group, an alkyl phenyl group, a naphthyl group, an alkyl naphthyl group, a biphenyl group and an alkyl biphenyl group as the aryl group.

In the cyanate ester compound represented by the formula (1), n is an integer of from 1 to 50.

The cyanate ester compound represented by the formula (1) is preferably a cyanate ester compound represented by any one of the formulae (2) to (4), more preferably a cyanate ester compound represented by any one of the formulae (5) to (7). In the cyanate ester compound represented by the formula (2), $R_1$ to $R_4$ are the same or different and represent hydrogen or an alkyl group, preferably an alkyl group having 1 to 4 carbon atoms, n is an integer of 1 to 50, and the position of each substituent of aromatic rings can be arbitrarily selected.

In the cyanate ester compound represented by the formula (3), $R_1$ to $R_4$ are the same or different and represent hydrogen or an alkyl group, preferably an alkyl group having 1 to 4 carbon atoms, n is an integer of 1 to 50, and the position of each substituent of aromatic rings can be arbitrarily selected.

In the cyanate ester compound represented by the formula (4), $R_1$ and $R_2$ are the same or different and represent hydrogen or an alkyl group, preferably an alkyl group having 1 to 4 carbon atoms, n is an integer of 1 to 50, and the position of each substituent of aromatic rings can be arbitrarily selected.

The process for the production of the compound of the formula (1), including the compounds of the formulae (2) to (7), is not specially limited and may be selected from all processes which are present as a cyanate synthesis.

For example, IAN HAMERTON, "Chemistry and Technology of Cyanate Ester Resins", BLACKIE ACADEMIC & PROFESSIONAL, discloses a synthesis process for general cyanate ester compounds. U.S. Pat. No. 3,553,244 provides a method in which a reaction is carried out in a solvent in the presence of a base such that cyanogen halide is always present in an excessive amount based on the base. JP-A-7-53497 discloses a method in which a synthesis is carried out with using a tertiaryamine as a base in an excessive amount based on cyanogen chloride. Japanese Kohyo No. 2000-501138 discloses a method which carries out a reaction between trialkylamine and cyanogen halide according to a continuous plug flow method. Japanese Kohyo No. 2001-504835 discloses a method in which tert-ammonium halide, which is a by-product obtained in a reaction between phenol and a cyanogen halide in a nonaqueous solution in the presence of a tert-amine, is treated with a cation and anion exchange-couple. Further, Japanese Patent No. 2991054 discloses a method in which a tertiary amine and cyanogen halide are concurrently added to a phenol compound in the presence of a solvent separable from water to allow them to react, washing with water and liquid separation are carried out, and purification by precipitation from the thus-obtained solution is carried out by using a poor solvent such as a secondary or tertiary alcohol or a hydro carbon.

The compound of the formula (1) can be obtained by reacting a phenol compound represented by the formula (8) with cyanogen chloride in a solvent in the presence of a basic compound. Further, there can be adopted a synthesis method in which a salt of the phenol compound of the formula (8) and a basic compound is formed in a solution containing water and then the salt is reacted with cyanogen chloride by a two-phase interface reaction to synthesize the compound of the formula (1).

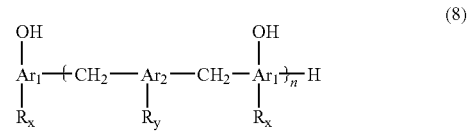

wherein $Ar_1$, $Ar_2$, $R_x$, $R_y$ and n are as defined in the formula (1).

As a general synthesis procedure of cyanate ester, the phenol compound of the formula (8) is dissolved in an organic solvent, a basic compound such as a tertiary amine is added and then the resultant mixture is reacted with an excessive amount of a cyanogen halide. In this system, since the cyanogen halide is always present in an excessive amount, it is said to be possible to inhibit imidocarbonate, which is to be generated by a reaction between phenolate anion and cyanate ester. However, since the excessive cyanogen halide reacts with the tertiary amine to generate dialkyl cyanamide, it is necessary to keep the reaction temperature at 10° C. or less, preferably 0° C. or less, more preferably −10° C. or less.

Other than the above method, the order of addition in the reaction, etc., maybe arbitrarily selected. For example, after the phenol compound is dissolved in solvent, a basic compound such as a tertiary amine and cyanogen halide or its solution may be alternately dropwise added or may be currently supplied. Further, a mixture solution of the phenol compound and a basic compound such as a tertiary amine and cyanogen halide or its solution may be concurrently supplied. In each case, the reaction is a large exothermic reaction, while it is necessary to keep the reaction temperature at 10° C. or less, preferably 0° C. or less, more preferably −10° C. or less, for the purpose of inhibiting a side reaction, etc.

The reaction may be carried out in any form. It may be a batch reaction, a semibatch reaction or a continuous flow reaction.

The basic compound such as a tertiary amine and the cyanogen halide are added in a total amount of 0.1 to 8 mole, preferably 1 to 3 mol, per 1.0 mol of a phenolic hydroxyl group of the phenol compound. In particular, when the phenol compound has a substituent having a steric hindrance at the ortho position of hydroxyl group, the total amount of the basic compound such as a tertiary amine and the cyanogen halide needed is increased as compared with a case where such a substituent is not present.

The cyanogen halide to be used is typically cyanogen chloride, cyanogen bromide, etc.

In the phenol compound represented by the formula (8), as the phenol compound to be used, $Ar_2$ represents a phenylene group, a naphthylene group or a biphenylene group, and $Ar_1$ represents a naphthylene group or a biphenylene group when $Ar_2$ is a phenylene group, or $Ar_1$ represents a phenylene group, a naphthylene group or a biphenylene group when $Ar_2$ is an aphthylene group or a biphenylene group. Specific examples of $Ar_1$ and $Ar_2$ include 1,4-phenylene group, 1,3-phenylene group, 4,41-biphenylene group, 2,4'-biphenylene group, 2,2'-biphenylene group, 2,3'-biphenylene group, 3,3'-biphenylene group, 3,4'-biphenylene group, 2,6-naphthylene group, 1,5-naphthylene group, 1,6-naphthylene group, 1,8-naphthylene group, 1,3-naphthylene group and 1,4-naphthylene group. $R_x$ represents all substituents of $Ar_1$, and each $R_x$ is the same or different and represents hydrogen, an alkyl group or an aryl group. Specific examples of $R_x$ include a methyl group, an ethyl group, an isopropyl group, a n-butyl group, an i-butyl group, a tert-butyl group and an isomer pentyl group as the alkyl group and a phenyl group, an alkyl phenyl group, a naphthyl group, an alkyl naphthyl group, a biphenyl group and an alkyl biphenyl group as the aryl group. $R_y$ represents all substituents of $Ar_2$, and each $R_y$ is the same or different and represents hydrogen, an alkyl group or an aryl group. Specific examples of $R_y$ include a methyl group, an ethyl group, an isopropyl group, an n-butyl group, an i-butyl group, a tert-butyl group and an isomer pentyl group as the alkyl group and a phenyl group, an alkyl phenyl group, a naphthyl group, an alkyl naphthyl group, a biphenyl group and an alkyl biphenyl group as the aryl group. Further, n is an integer of from 1 to 50.

The compound of the formula (8) can be obtained by, for example, the methods disclosed in Japanese Patent No. 3122834 and Japanese Patent No. 2866747. Concretely, there are a method in which a bishalogenomethyl compound such as a compound represented by $Ar_2$—$(CH_2$—$X)_2$ is reacted with a phenol compound in the presence of an acid catalyst or in the absence of a catalyst, and a method in which a bis (alkoxymethyl) compound such as $Ar_2$—$(CH_2OR)_2$ or a bis (hydroxymethyl) compound such as $Ar_2$—$(CH_2OH)_2$ is reacted with a phenol compound in the presence of an acid catalyst.

The basic compound to be used is not specially limited and is selected from organic and inorganic bases. The organic base is preferably an organic base having a high solubility. Particularly, a tertiary amine with less side reaction is preferable. The tertiary amine is freely selected from alkyl amines, aryl amines and cycloalkyl amines. Specific examples thereof include trimethylamine, triethylamine, methyldiethylamine, tripropylamine, tributylamine, methyldibutylamine, dinonylmethylamine, dimethylstearylamine, dimethylcyclohexylamine, diethylaniline, pyridine and quinoline.

The solvent to be used for the reaction includes ketone solvents such as acetone, methyl ethyl ketone and methyl isobutyl ketone, aromatic solvents such as benzene, toluene and xylene, ether solvents such as diethyl ether, dimethylcellosolve, diglyme, tetrahydrofuran, methyltetrahydrofuran, dioxane and tetraethyleneglycoldimethylether, halogenated hydrocarbon solvents such as methylene chloride, chloroform, carbon tetrachloride and chlorobenzene, alcohol solvents such as methanol, ethanol, isopropanol, methylcellosolve and propyleneglycolmonomethylether, aprotic polar solvents such as N,N-dimethylformamide, N-methylpyrrolidone, 1,3-dimethyl-2-imidazolidone and dimethyl sulfoxide, nitrile solvents such as acetonitrile and benzonitrile, nitro solvents such as nitromethane and nitrobenzene, ester solvents such as ethyl acetate and ethyl benzoate, hydrocarbon solvents such as cyclohexane. These solvents may be used alone or in combination in accordance with a reactant.

As a post-treatment after the reaction, generally, a hydrochloric salt of the basic compound such as a tertiary amine, which is a by product, is removed by filtration or washing with water. Taking the washing with water into consideration, it is preferable to use a solvent which is not miscible with water in the reaction. Further, there is adopted a method using an acidic aqueous solution such as a dilute hydrochloric acid for removing excess amines in the washing step. For removing a water content from a sufficiently-washed reaction liquid, it is possible to carry out a drying operation by a general method such as sodium sulfate or magnesium sulfate.

After these operations, a concentration operation, a precipitation operation or a crystallization operation is carried out. For the concentration, since the cyanate ester compound has an unstable structure, a pressure reduction is carried out with keeping 150° C. or lower. For the precipitation or the crystallization, a solvent having a low solubility can be used. For example, an ether solvent, a hydrocarbon solvent such as hexane or an alcohol solvent may be dropwise added to the reaction solution. Otherwise, the reaction solution may be inversely dropwise added.

For washing a crude product obtained, there can be adopted a method in which a concentrate of the reaction solution or a precipitated crystal is washed with an ether solvent, a hydrocarbon solvent such as hexane or an alcohol solvent. Further, a crystal obtained by concentrating the reaction solution may be again dissolved and then recrystallized. Further, when crystallization is carried out, the reaction solution may be simply concentrated or cooled. By removing volatile contents from the thus-obtained product according to a method such as drying under reduced pressure, there can be obtained a high-purity cyanate ester compound.

Then, the curable resin composition of the present invention will be explained. The above curable resin composition is characterized by containing the aforementioned cyanate ester compound of the present invention. The curable resin composition of the present invention may contain a cyanate ester compound other than the cyanate ester compound of the present invention, an epoxy resin, an oxetane resin and/or a compound having a polymerizable unsaturated group.

The cyanate ester compound other than the cyanate ester compound of the present invention can be selected from known cyanate ester compounds. Examples of thereof include bisphenol A dicyanate, bisphenol F dicyanate, bisphenol M dicyanate, bisphenol P dicyanate, bisphenol E dicyanate, phenol novolak type cyanate, cresol novolak type cyanate, dicyclopentadiene novolak type cyanate, tetramethyl bisphenol F dicyanate and biphenol dicyanate. These cyanate ester compounds may be used alone or in combination.

When the cyanate ester compound is cured, a known curing catalyst may be used. Examples thereof include metal salts such as zinc octylate, zinc naphthenate, cobalt naphthenate, copper naphthenate and acetylacetone iron, and compounds having an active hydroxyl group such as phenol, an alcohol and an amine.

The epoxy resin can be selected from known epoxy resins. Examples thereof include a bisphenol A type epoxy resin, a bisphenol F type epoxy resin, a biphenyl type epoxy resin, a phenol novolak type epoxy resin, a cresol novolak type epoxy resin, a xylene novolak type epoxy resin, triglycidyl isocyanurate, an alicyclic epoxy resin, a dicyclopentadiene. novolak type epoxy resin, a biphenyl aralkyl novolak type epoxy resin, a phenol aralkyl novolak type epoxy resin, a naphthol aralkyl novolak type epoxy resin, a bisphenol A novolak type epoxy resin, a brominated bisphenol A type epoxy resin, a brominated phenol novolak type epoxy resin, a trifunctional phenol type epoxy resin, a tetrafunctional phenol type epoxy resin, a naphthalene type epoxy resin and a phosphorus-containing epoxy resin. Preferred examples thereof include a bisphenol A type epoxy resin, a bisphenol F type epoxy resin, a phenol novolak type epoxy resin, a cresol novolak type epoxy resin, a bisphenol A novolak type epoxy resin, a brominated bisphenol A type epoxy resin, a brominated phenol novolak type epoxy resin, a biphenyl type epoxy resin, a phenol aralkyl novolak type epoxy resin, a biphenyl aralkyl novolak type epoxy resin and a naphthol aralkyl novolak type epoxy resin. These epoxy resins may be used alone or in combination. The amount of the epoxy resin is not specially limited. The amount of the epoxy resin is preferably 10 to 90% by weight, particularly preferably 30 to 70% by weight, based on the total amount of the cyanate ester compound and the epoxy resin.

The oxetane resin can be selected from generally known oxetane resins. Examples thereof include alkyl oxetanes such as oxetane, 2-methyloxetane, 2,2-dimethyloxetane, 3-methyloxetane and 3,3-dimethyloxetane, 3-methyl-3-methoxymethyloxetane, 3,3'-di(trifluoromethyl)perfluoxetane, 2-chloromethyloxetane, 3,3-bis(chrolomethyl)oxetane, OXT-101 (tradename, supplied by TOAGOSEI Co., Ltd.) and OXT-121 (trade name, supplied by TOAGOSEI Co., Ltd.). These oxetane resins may be used alone or in combination.

When the curable resin composition of the present invention contains the epoxy resin and/or the oxetane resin, an epoxy resin curing agent and/or an oxetane resin curing agent may be used. The above epoxy resin curing agent can be selected from generally known epoxy resin curing agents. Examples thereof include imidazole derivatives such as 2-methylimidazole, 2-ethyl-4-methylimidazole, 2-phenylimidazole, 1-cyanoethyl-2-phenylimidazole, 1-cyanoethyl-2-ethyl-4-methylimidazole, 2-phenyl-4,5-dihydroxymethylimidazole and 2-phenyl-4-methyl-5-hydroxymethylimidazole; amine compounds such as dicyandiamide, benzyldimethylamine and 4-methyl-N,N-dimethylbenzylamine; and phosphine compounds such as phosphonium compounds. The oxetane resin curing agent can be selected from known cationic polymerization initiators. Commercially available examples include SAN-AID SI-60L, SAN-AID SI-80L, SAN-AID SI-100L (supplied by Sanshin Chemical Industry Co., Ltd.), CI-2064 (supplied by Nippon Soda Co., Ltd.), IRGACURE261 (supplied by Ciba Specialty Chemicals), ADEKAOPTMER SP-170, ADEKAOPTMER SP-150, (supplied by Asahi Denka Kogyo K.K.), and CYRACURE UVI-6990 (supplied by Union Carbide Corporation). The cationic polymerization initiators can be used as the epoxy resin curing agent. These curing agents may be used alone or in combination.

The compound having a polymerizable unsaturated group can be selected from generally known compounds having a polymerizable unsaturated group. Examples thereof include vinyl compounds such as ethylene, propylene, styrene, divinyl benzene and divinyl biphenyl; (meth)acrylates of monohydric and polyhydric alcohols such as methyl(meth)acrylate, 2-hydroxyethyl (meth) acrylate, 2-hydroxypropyl(meth)acrylate, polypropylene glycol di(meth)acrylate, trimethylol propane di(meth)acrylate, trimethylol propane tri(meth)acrylate, pentaerythritol tetra(meth)acrylate and dipentaerythritol hexa(meth)acrylate; epoxy (meth)acrylates such as a bisphenol A type epoxy (meth)acrylate and a bisphenol F type epoxy (meth)acrylate; a benzocyclobutene resin and a maleimide compound. These compounds having an unsaturated group may be used alone or in combination.

The maleimide compound can be selected from known maleimide compounds. Examples thereof include bis(4-maleimidephenyl)methane, 2,2-bis{4-(4-maleimidephenoxy)-phenyl}propane, bis(3,5-dimethyl-4-maleimidephenyl)methane, bis(3-ethyl-5-methyl-4-maleimidephenyl)methane, bis(3,5-diethyl-4-maleimidephenyl)methane, polyphenyl methane maleimide, prepolymers of these maleimide compounds and a prepolymer of maleimide compound and an amine compound. These maleimide compounds may be used alone or in combination. The maleimide compound is preferably bis(4-maleimidephenyl)methane, 2,2-bis{4-(4-maleimidephenoxy)-phenyl}propane or bis(3-ethyl-5-methyl-4-maleimidephenyl)methane. The amount of the maleimide compound is not specially limited. The amount of the maleimide compound is preferably 5 to 75% by weight, particularly preferably 10 to 70% byweight, based on the total amount of the cyanate ester compound and the maleimide compound.

When the compound having an unsaturated group is used, a known polymerization initiator may be used as required. The polymerization initiator can be selected from known polymerization initiators. Examples thereof include peroxides such as benzoyl peroxide, p-chlorobenzoyl peroxide, di-t-butylperoxide, diisopropyl peroxycarbonate and di-2-ethylhexylperoxycarbonate, and azo compounds such as azobisisobutylonitrile.

Further, when the curable resin composition of the present invention is produced, there may be added a known additive such as a thermoplastic resin, an inorganic filler, a color pigment, an antifoamer, a surface conditioner, a flame retardant, an ultraviolet absorber, an antioxidant and a flow regulator, as required. Examples of the inorganic filler include silicas such as natural silica, fused silica, amorphous silica and hollow silica, white carbon, titanium white, aerosil, alumina, talc, natural mica, synthetic mica, kaolin, clay, calcined clay, calcined kaolin, calcined talc, mica; metal hydrates such as aluminum hydroxide, heat-treated aluminum hydroxide (obtained by heat-treating aluminum hydroxide and reducing part of crystal water), boehmite and magnesium hydroxide; molybdenum compounds such as molybdenum oxide and zinc molybdate, zinc borate, zinc stannate, barium sulfate, E-glass, A-glass, NE-glass, C-glass, L-glass, D-glass, S-glass, M-glass G20 and hollow glass. The average particle diameter of the inorganic filler is preferably 0.1 to 10 μm. Inorganic fillers having different particle size distributions or different average particle diameters may be used in combination as required. The amount of the inorganic filler is not specially limited. The amount of the inorganic filler per 100 parts by weight of the resin component of the resin composition is preferably 10 to 300 parts by weight, particularly preferably 30 to 200 parts by weight.

An organic solvent may be used in combination with the resin composition of the present invention as required. The organic solvent is not specially limited so long as it can compatibly dissolve a mixture of the cyanate ester resin and the epoxy resin or the maleimide compound. Specific examples thereof include ketones such as acetone, methyl ethyl ketone, methyl isobutyl ketone and cyclohexanone, aromatic hydrocarbons such as benzene, toluene and xylene, and amides such as dimethylformamide and dimethylacetamide.

The base material used in the present invention can be selected from known base materials which are used for various printed wiring board materials. Examples thereof include inorganic fibers such as E glass, D glass, S glass, NE glass and quartz, and organic fibers such as polyimide, polyamide and polyester. The base material is properly selected according to intended use or performance as required. These base materials maybe used alone or in combination. The form of the base material is typically a woven fabric, a nonwoven fabric, roving, a chopped strand mat or a surfacing mat. The thickness of the base material is not specially limited. Generally, it is about 0.01 to 0.3 mm. Further, base materials surface-treated with a silane-coupling agent or the like and physically-opening-treated woven fabrics can be preferably used in view of heat resistance after moisture absorption. Further, a film of polyimide, polyamide, polyester or the like may be also used. The thickness of the film is not specially limited and it is preferably about 0.002 to 0.05 mm. A film surface-treated by plasma treatment or the like is more referred.

The process for producing the prepreg of the present invention is not specially limited so long as it is a process in which prepreg is produced by combining the resin composition and the base material. For example, it is typically a method in which the above resin composition is impregnated into or applied to the base material, and then the impregnated or applied resin composition is semi-cured by, for example, heating it in a dryer at 100 to 200° C. for 1 to 60 minutes, to produce a prepreg. The total amount of the resin and inorganic filler of the resin composition in the prepreg is preferably 20 to 95% by weight based on the base material.

The laminate of the present invention is obtained by laminate-molding using the above prepreg. Specifically, the laminate of the present invention is produced by placing one sheet of the above prepreg or stacking two or more sheets of the prepregs, disposing metal foil(s) such as a copper foil or an aluminum foil on one surface or both surfaces of the prepreg or the stacked prepregs, as required, and laminate-molding the resultant set. The metal foil used is not specially limited so long as it is selected from metal foils which are used for printed wiring board materials. As for molding conditions, general techniques for laminates and multilayer boards for printed wiring boards can be used. For example, a multiplaten press, a multiplaten vacuum press, continuous molding, an autoclave molding machine or the like is generally used, the temperature is generally from 100 to 300° C., the pressure is generally from 2 to 100 kgf/cm$^2$, and the heating time is generally from 0.05 to 5 hours. Further, it is also possible to produce a multilayer board by combining the prepreg of the present invention with an internal layer wiring board which is separately prepared and laminate-molding the resultant set.

The cured product of the present invention can be obtained by curing the curable resin composition of the present invention, obtained by the above process, under heat. When the curing temperature is too low, the curable resin composition does not undergo curing. When it is too high, the cured product deteriorates. Therefore, the curing temperature is preferably in the range of from 150° C. to 300° C.

The so-obtained resin composition is suitable for various applications such as an electrical insulating material, a resin for a resist, a semiconductor-sealing resin, an adhesive for a printed wiring board, a buildup laminate material, a resin for fiber-reinforced plastics, a sealing resin for a liquid crystal display panel, a resin for a color filter of liquid crystal, a coating composition, various coating agents and an adhesive.

The present invention will be explained more concretely with reference to Examples hereinafter, while the present invention shall not be specially limited to these Examples.

EXAMPLES

Example A1

Synthesis of cyanate ester of biphenyl novolak (Formula (9): to be Referred to as "G65C")

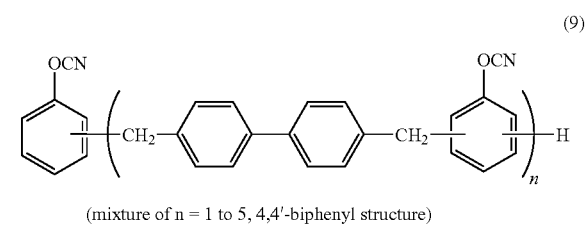

(mixture of n = 1 to 5, 4,4'-biphenyl structure)

Biphenyl novolak having 1.1 mol of OH groups (supplied by Nippon Kayaku Co., Ltd., KAYAHARD-GPHG65) and 1.6 mol of triethylamine were dissolved in 900 ml of 3-methyltetrahydrofuran, to obtain a solution 1. The solution 1 was dropwise added to 2,500 g of a methylene chloride solution of 2.2 mol of cyanogen chloride at −10° C. over 1.5 hours. The mixture was stirred for 30 minutes. Then, a mixed solution of 0.4 mol of triethylamine and 100 g of methylene chloride was dropwise added, and the resultant mixture was further stirred for 30 minutes to complete the reaction. A hydrochloride of triethylamine was separated by filtration. The thus-obtained filtrate was washed with 1,000 ml of 0.1 N hydrochloric acid, and then washing with 1,000 ml of water was repeated four times. After drying with sodium sulfate, evaporation was carried out at 75° C., to obtain a crystal of a yellow solid. The crystal was washed with diethyl ether and hexane and then dried under a reduced pressure, to obtain a cyanate ester G65C of biphenyl novolak. Identification was carried out by an infrared absorption spectrum measurement.

Example B1-1

Production of Cured Product

The cyanate ester G65C of biphenyl novolak obtained in Example 1 in an amount shown in Table 1 was added in a short-neck flask. The cyanate ester G65C was molten under heat at 150° C. and degassed with a vacuum pump. Then, zinc octylate was added and the resultant mixture was stirred for 1 minute. The stirred mixture was casted in a mold composed of a glass plate (120 mm×120 mm×5 mmt), a polyimide film (Kapton 200H: DU PONT—TORAY CO.,LTD.) and an O-ring made of fluoro rubber (S-100: MORISEI Co., Ltd.), and it was cured by heating in an oven at 170° C. for 1 hour and at 230° C. for 9 hours. After cooling, the polyimide film was removed by polishing to obtain a cured product of cyanate ester compound.

The obtained cured product was evaluated for properties by the following methods.

Glass transition temperature (Tg): Obtained according to a dynamic viscoelasticity measurement (DMA). The measurement was carried out at an oscillation frequency of 10 GHz.

Dielectric constant and dielectric loss tangent: Obtained according to a cavity resonant oscillation method.

Flame resistance: A flame resistance test was carried out according to UL94. The size of a sample was 10 mm×70 mm×1.5 mm.

Table 1 shows the evaluation results of physical properties.

Example B1-2

A cured product was obtained in the same manner as in Example B1-1 except that 50 parts by weight of the G65 C obtained in Example 1 and 50 parts by weight of bisphenol A dicyanate Skylex, supplied by Mitsubishi Gas Chemical Company, Inc., were used.

Table 1 shows the evaluation results of physical properties of the cured product.

Comparative Example B1

A cured product was obtained in the same manner as in Example B1-1 except that the G65C was replaced with bisphenol Adicyanate Skylex, supplied by Mitsubishi Gas Chemical Company, Inc., alone.

Table 1 shows the evaluation results of physical properties of the cured product.

Comparative Example B2

A cured product was obtained in the same manner as in Example B1-1 except that the G65C was replaced with phenol novolak cyanate PT 30 supplied by LONZA.

Table 1 shows the evaluation results of physical properties of the cured product.

TABLE 1

| | | Example B1-1 | Example B1-2 | Comparative Example B1 | Comparative Example B2 |
|---|---|---|---|---|---|
| Mixing amount (Part by weight) | G65C | 100 | 50 | — | — |
| | Bisphenol A dicyanate | — | 50 | 100 | — |
| | Phenol novolak cyanate | — | — | — | 100 |
| | Zinc octylate | 0.05 | 0.05 | 0.05 | 0.05 |
| Properties | Tg (° C.: DMA) | 259 | 283 | 304 | 286 |
| | Dielectric constant (10 GHz) | 2.79 | 2.76 | 2.73 | 3.02 |
| | Dielectric loss tangent (10 GHz) | 0.005 | 0.007 | 0.011 | 0.015 |
| | Flame resistance (UL94) | V-0 | V-1 | Entirely burned | Entirely burned |

Example A2

Synthesis of Cyanate ester of biphenyl novolakmonomer (Formula (10): to be Referred to as "BPN-CN")

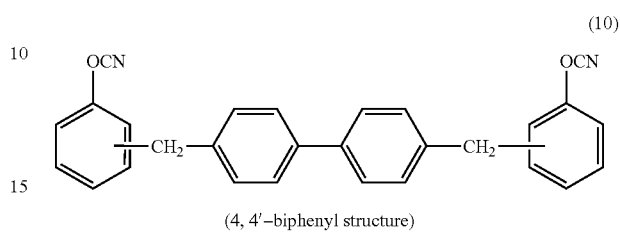

(4, 4'–biphenyl structure)

A biphenyl novolak monomer having 0.4 mol of OH groups and 0.4 mol of triethylamine were dissolved in 600 ml of 3-methyltetrahydrofuran, to obtain a solution 1. The solution 1 was dropwise added to a mixed solution of 220 g of a methylene chloride solution of 0.8 mol of cyanogen chloride and 400 g of 3-methyltetrahydrofuran at −10° C. over 1.5 hours. Themixture was stirred for 30 minutes. Then, a mixed solution of 0.32 mol of triethylamine and 80 g of 3-methyltetrahydrofuran was dropwise added, and the resultant mixture was further stirred for 30 minutes to complete the reaction. A hydrochloride of triethylamine was separated by filtration. The thus-obtained filtrate was washed with 1,000 ml of 0.1 N hydrochloric acid, and then washing with 1,000 ml of water was repeated four times. After drying with sodium sulfate, evaporation was carried out at 75° C., to obtain a crystal of a yellow solid. The crystal was washed with diethyl ether and hexane and then dried under a reduced pressure, to obtain a cyanate ester BPN-CN of biphenyl novolak monomer. Identification was carried out by an infrared absorption spectrum measurement.

Example A3

2,6-bis(4-cyanate-3,5-dimethylphenylmethyl)naphthalene (formula (11): to be Referred to as "26XNDC")

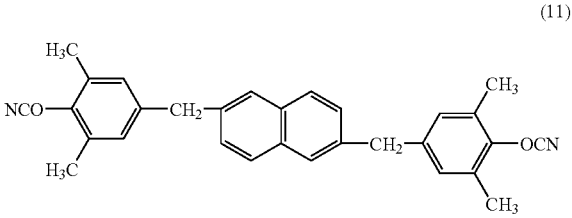

0.4 mol of 2,6-bis(4-phenoxy-3,5-dimethylphenylmethyl) naphthalene and 1.3 mol of triethylamine were dissolved in 600 ml of 3-methyltetrahydrofuran, to obtain a solution 1. The solution 1 was dropwise added to a mixed liquid of 2,500 g of a methylene chloride solution of 2 mol of cyanogen chloride and 1,000 g of chloroform at −10° C. over 1.5 hours. The mixture was stirred for 30 minutes. Then, a mixed solution of 0.6 mol of triethylamine and 100 g of methylene chloride was dropwise added, and the resultant mixture was further stirred for 30 minutes to complete the reaction. The reaction liquid was filtered. Then, the thus-obtained filtrate was washed with 1,000 ml of 0.1 N hydrochloric acid, and then washing with 1,000 ml of water was repeated four times. After drying with sodium sulfate, a concentration operation was carried out at 75° C. As the concentration operation advanced, a white crystal precipitated. The white crystal was washed with diethyl ether and hexane and then dried under a reduced pressure, to obtain a white crystal, 2,6-bis(4-cyanate-3,5-dimethylphenylmethyl)naphthalene (26XNDC). Identification was carried out by an infrared absorption spectrum measurement.

Example A4

Synthesis of Cyanate ester of naphthol aralkyl (Formula (12): to be Referred to as "SN485CN")

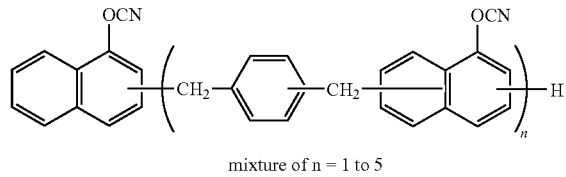

(12)

mixture of n = 1 to 5

Naphtholaralkyl having 0.47 mol of OH groups (supplied by Nippon Steel Chemical Co., Ltd., SN485N) and 0.7 mol of triethylamine were dissolved in 500 ml of chloroform, to obtain a solution 1. The solution 1 was dropwise added to 300 g of a chloroform solution of 0.93 mol of cyanogen chloride at −10° C. over 1.5 hours. The mixture was stirred for 30 minutes. Then, a mixed solution of 0.1 mol of triethylamine and 30 g of chloroform was dropwise added, and the resultant mixture was further stirred for 30 minutes to complete the reaction. The thus-obtained reaction liquid was washed with 500 ml of 0.1 N hydrochloric acid, and then washing with 500 ml of water was repeated four times. After drying with sodium sulfate, evaporation was carried out at 75° C., to obtain a brown solid. The solid was washed with diethyl ether and hexane and then dried under a reduced pressure, to obtain a cyanate ester of naphthol aralkyl. Identification was carried out by an infrared absorption spectrum measurement.

Example B2

A cured product was obtained in the same manner as in Example B1-1 except that the G65C was replaced with BPN-CN obtained in Example A2.

Table 2 shows the evaluation results of physical properties of the cured product.

Example B3

A cured product was obtained in the same manner as in Example B1-1 except that the G65C was replaced with a mixture of 50 parts by weight of 26XNDC obtained in Example A3 and 50 parts by weight of bisphenol A dicyanate Skylex, supplied by Mitsubishi Gas Chemical Company, Inc.

Table 2 shows the evaluation results of physical properties of the cured product.

Example B4

A cured product was obtained in the same manner as in Example B1-1 except that the G65C was replaced with SN485CN obtained in Example A4.

Table 2 shows the evaluation results of physical properties of the cured product.

TABLE 2

|  |  | Example B2 | Example B3 | Example B4 |
|---|---|---|---|---|
| Mixing amount (Part by weight) | BPN-CN | 100 | — | — |
|  | 26XNDC | — | 50 | — |
|  | SN485CN | — | — | 100 |
|  | Bisphenol A dicyanate | — | 50 | — |
|  | Zinc octylate | 0.05 | 0.05 | 0.05 |
| Properties | Tg (° C.: DMA) | 231 | 276 | 274 |
|  | Dielectric constant (10 GHz) | 2.77 | 2.7 | 2.86 |
|  | Dielectric loss tangent (10 GHz) | 0.004 | 0.007 | 0.004 |
|  | Flame resistance (UL94) | V-0 | V-0 | V-0 |

Example C1

70 parts by weight of the cyanate ester of naphthol aralkyl obtained in Example A4 and 30 parts by weight of a bisphenol A type epoxy resin (Epikote 1001, supplied by Japan Epoxy Resins Co., Ltd.) were dissolved in methyl ethyl ketone and 0.04 part by weight of zinc octylate was mixed with the resultant solution to obtain a varnish. The varnish was diluted with a methyl ethyl ketone solvent, the diluted varnish was impregnated into an E glass cloth having a thickness of 0.1 mm, and the impregnated varnish was dried under heat at 160° C. for 4 minutes, to obtain prepregs having a resin content of 41% by weight. Four said prepregs were stacked and 18 μm-thick electrolytic copper foils were placed on the upper and lower surfaces of the stacked prepregs, one copper foil on the upper surface and one copper foil on the lower surface, and the resultant set was pressed at a pressure of 30 kgf/cm$^2$ at a temperature of 220° C. for 120 minutes, to obtain a copper-clad laminate having a thickness of 0.4 mm. Table 3 shows the measurement results of physical properties of the thus-obtained copper-clad laminate.

Example C2

30 parts by weight of the cyanate ester of naphthol aralkyl obtained in Example A4, 45 parts by weight of a brominated phenol novolak type epoxy resin (BREN-S, supplied by Nippon Kayaku Co., Ltd.) and 25 parts by weight of a cresol novolak type epoxy resin (ESCN-220F, supplied by Sumitomo Chemical Co. Ltd.) were dissolved in methyl ethyl ketone, and 0.04 part by weight of zinc octylate was mixed with the resultant solution to obtain a varnish. Then, prepregs having a resin content of 43% by weight were obtained in the same manner as in Example C1 except that the above varnish was used. The procedures thereafter were carried out in the same manner as in Example C1, to obtain a copper-clad laminate having a thickness of 0.4 m. Table 3 shows the measurement results of physical properties f the thus-obtained copper-clad laminate.

Example C3

50 parts by weight of the cyanate ester of naphthol aralkyl obtained in Example A4 and 50 parts by weight of a biphenyl aralkyl novolak type epoxy resin (NC-3000H, supplied by Nippon Kayaku Co., Ltd.) were dissolved in methyl ethyl ketone and. 0.04 part by weight of zinc octylate was mixed with the resultant solution to obtain a varnish. Then, prepregs having a resin content of 41% by weight were obtained in the same manner as in Example C1 except that the above varnish was used. The procedures thereafter were carried out in the same manner as in Example C1, to obtain a copper-clad laminate having a thickness of 0.4 mm. Table 3 shows the measurement results of physical properties of the thus-obtained copper-clad laminate.

Comparative Example C1

A copper-clad laminate having a thickness of 0.4 mm was obtained in the same manner as in Example C1 except that 70 parts by weight of the cyanate ester of naphthol aralkyl used in Example C1 was replaced with 70 parts by weight of a prepolymer (BT2070, supplied by Mitsubishi Gas Chemical Company, Inc.) of a bisphenol A dicyanate ester. Table 3 shows the measurement results of physical properties of the thus-obtained copper-clad laminate.

Comparative Example C2

A copper-clad laminate having a thickness of 0.4 mm was obtained in the same manner as in Example C1 except that 70 parts by weight of the cyanate ester of naphthol aralkyl used in Example C1 was replaced with 70 parts by weight of a phenol novolak type cyanate ester (Primaset PT-30, supplied by LONZA). Table 3 shows the measurement results of physical properties of the thus-obtained copper-clad laminate.

Example C4

70 parts by weight of the cyanate ester of naphthol aralkyl obtained in Example A4, 30 parts by weight of a phenol novolak type epoxy resin (EPICLON N-770), 1 part by weight of a silane-coupling agent (silane A187, supplied by Nihon Yunika) and 1 part by weight of a wetting and dispersing agent (BYK-W903, supplied by Big Chemie Japan) were dissolved and mixed in methyl ethyl ketone, and 100 parts by weight of aluminum hydroxide (CL-303, supplied by Sumitomo Chemical Co. Ltd.) and 0.04 part by weight of zinc octylate were further mixed with the resultant solution, to obtain a varnish. The varnish was diluted with methyl ethyl ketone, the diluted varnish was impregnated into an E glass cloth having a thickness of 0.1 mm, and the impregnated varnish was dried under heat at 160° C. for 4 minutes, to obtain prepregs having a resin content of 48% by weight. The procedures thereafter were carried out in the same manner as in Example C1, to obtain a copper-clad laminate having a thickness of 0.4 mm. Table 4 shows the measurement results of physical properties of the thus-obtained copper-clad laminate.

Example C5

50 parts by weight of the cyanate ester of naphthol aralkyl obtained in Example A4, 50 parts by weight of a biphenyl aralkyl novolak type epoxy resin (NC-3000-H), 1 part by weight of a silane-coupling agent (silane A187) and 1 part by weight of a wetting and dispersing agent (BYK-W903) were dissolved and mixed in methyl ethyl ketone. Further, 30 parts by weight of heat-treated aluminum hydroxide (BS40, boehmite conversion rate: 40%, supplied by Kawai Lime Industry Co. Ltd.), 20 parts by weight of boehmite (BS100, supplied by Kawai Lime Industry Co. Ltd.), 3 parts by weight of talc coated with zinc molybdate (Kemgard 911C, zinc molybdate support: 10% by weight, supplied by Sherwin Williams) and 0.01 part by weight of zinc octylate were mixed with the resultant solution to obtain a varnish. The varnish was diluted with methyl ethyl ketone, the diluted varnish was impregnated into an E glass cloth having a thickness of 0.1 mm, and the impregnated varnish was dried under heat at 160° C. for 3 minutes, to obtain prepregs having a resin content of 47% by weight. The procedures thereafter were carried out in the same manner as in Example C1, to obtain a copper-clad laminate having a thickness of 0.4 mm. Table 4 shows the measurement results of physical properties of the thus-obtained copper-clad laminate.

Example C6

40 parts by weight of the cyanate ester of naphthol aralkyl obtained in Example A4, 50 parts by weight of a phosphorus-containing epoxy resin (FX-305, supplied by Tohto Kasei Co., Ltd.), 10 parts by weight of aphenol aralkyl novolak type epoxy resin (E-XLC-LL, supplied by Mitsui Chemicals, Inc.) and 1 part by weight of a silane-coupling agent (silane A187) were dissolved and mixed in methyl ethyl ketone. Further, 50 parts by weight of calcined talc (BST-200L, supplied by NIPPON TALC CO., LTD.) and 0.04 part by weight of zinc octylate were mixed with the resultant solution to obtain a varnish. The varnish was diluted with methyl ethyl ketone, the diluted varnish was impregnated into an E glass cloth having a thickness of 0.1 mm, and the impregnated varnish was dried under heat at 160° C. for 3 minutes, to obtain prepregs having a resin content of 47% by weight. The procedures thereafter were carried out in the same manner as in Example C1, to obtain a copper-clad laminate having a thickness of 0.4 mm. Table 4 shows the measurement results of physical properties of the thus-obtained copper-clad laminate.

Example C7

50 parts by weight of the cyanate ester of naphthol aralkyl obtained in Example A4, 50 parts by weight of a biphenyl aralkyl novol aktypeepoxy resin (NC-3000-H) and part by weight of a silane-coupling agent (silane A187) were dissolved and mixed in methyl ethyl ketone. Further, 150 parts by weight of spherical synthetic silica (SC-2050, supplied by ADMATECHS CO., LTD) and 0.04 part by weight of zinc octylate were mixed with the resultant solution to obtain a varnish. The varnish was diluted with methyl ethyl ketone, the diluted varnish was impregnated into an E glass cloth having a thickness of 0.1 mm, and the impregnated varnish was dried under heat at 160° C. for 5 minutes, to obtain prepregs having a resin content of 47% by weight. The procedures thereafter were carried out in the same manner as in Example C1, to obtain a copper-clad laminate having a thickness of 0.4 mm. Table 4 shows the measurement results of physical properties of the thus-obtained copper-clad laminate.

Comparative Example C3

A copper-clad laminate having a thickness of 0.4 mm was obtained in the same manner as in Example C5 except that 50 parts by weight of the cyanate ester of naphthol aralkyl used in Example CS was replaced with 50 parts by weight of a prepolymer (BT2070) of bisphenol A dicyanate ester. Table 4 shows the measurement results of physical properties of the thus-obtained copper-clad laminate.

Comparative Example C4

A copper-clad laminate having a thickness of 0.4 mm was obtained in the same manner as in Example C5 except that 50 parts by weight of the cyanate ester of naphthol aralkyl used in Example C5 was replaced with 50 parts by weight of a phenol novolak type cyanate ester (Primaset PT-30). Table 4 shows the measurement results of physical properties of the thus-obtained copper-clad laminate.

TABLE 3

| | | Ex. C1 | Ex. C2 | Ex. C3 | CEx. C1 | CEx. C2 |
|---|---|---|---|---|---|---|
| Copper foil peeling strength | | 1.1 | 1.1 | 1.2 | 1.0 | 0.9 |
| Glass transition temperature (° C.) | | 230 | 210 | 240 | 230 | 240 |
| Heat resistance after moisture absorption | | 0/4 | 0/4 | 0/4 | 2/4 | 4/4 |
| Water absorption coefficient (wt %) | | 0.5 | 0.5 | 0.4 | 0.9 | 1.1 |
| Insulation resistance ($\Omega$) | 100 hours | $5 \times 10^{13}$ | $4 \times 10^{15}$ | $3 \times 10^{14}$ | $3 \times 10^{11}$ | $2 \times 10^{9}$ |
| | 200 hours | $1 \times 10^{13}$ | $6 \times 10^{13}$ | $1 \times 10^{14}$ | $5 \times 10^{10}$ | $8 \times 10^{8}$ |

Ex. = Example, CEx. = Comparative Example

TABLE 4

| | Ex. C4 | Ex. C5 | Ex. C6 | Ex. C7 | CEx. C3 | CEx. C4 |
|---|---|---|---|---|---|---|
| Copper foil peeling strength | 1.1 | 1.2 | 1.1 | 1.1 | 1.0 | 0.9 |
| Insulation resistance ($\Omega$) | $1.4 \times 10^{10}$ | $2.8 \times 10^{11}$ | $4.2 \times 10^{10}$ | $2.9 \times 10^{11}$ | $5.1 \times 10^{8}$ | $5.7 \times 10^{7}$ |
| Water absorption coefficient (wt %) | 0.3 | 0.3 | 0.4 | 0.2 | 0.5 | 0.6 |
| Heat resistance after moisture absorption | 0/4 | 0/4 | 0/4 | 0/4 | 1/4 | 3/4 |
| Flame resistance | V-0 | V-0 | V-0 | V-0 | Burned | V-0 |

Ex. = Example, CEx. = Comparative Example (Measurement Methods)

1) Copper foil peeling strength: Measured according to JIS C6481 (unit: kgf/cm).

2) Glass transition temperature: Measured by DMA method according to JIS C6481.

3) Heat resistance after moisture absorption: The entire copper foil of a 50 mm×50 mm sample other than a copper foil on the half of one surface of the sample was removed by etching. The sample was treated with a pressure cooker testing machine (PC-3 type, supplied by Hirayama Manufacturing Corporation) at 121° C. at 2 atmospheric pressure for 3 hours, and then the sample was immersed in a solder at 260° C. for 30 seconds, to check an appearance change by visual observation. (number of swellings/number of tested samples).

4) Water absorption coefficient: A sample was treated with a pressure cooker testing machine (PC-3 type, supplied by Hirayama Manufacturing Corporation) at 121° C. at 2 atmospheric pressure for 3 hours according to JIS C6481, and then it was measured for a water absorption coefficient (in Table4, a water absorption coefficient measured after the sample was treated for 5 hours).

5) Insulation resistance: A sample was treated with a pressure cooker testing machine (PC-3 type, supplied by Hirayama Manufacturing Corporation) at 121° C. at 2 atmospheric pressure for a predetermined time according to JIS C6481, and then it was measured for insulation resistance (in Table 4, insulation resistance measured after the sample was treated for 500 hours).

6) Flame resistance: Measured according to a UL 94 vertical test method.

Example B5

70 parts by weight of the cyanate ester of naphthol aralkyl obtained in Example A4 and 30 parts by weight of bis(4-maleimidephenyl)methane (BMI-H, supplied-byKIKASEIKK) were melt-blended at 160° C. for 10 minutes. The melt-blended mixture was poured into a casting mold, defoamed under vacuum at 165° C. for 15 minutes and then cured under heat at 180° C. for 4 hours, at 200° C. for 4 hours, and at 250° C. for 4 hours, to obtain a cured product having a thickness of 3 mm and a cured product having a thickness of 4 mm. Table 5 shows the measurement results of the physical properties of the cured products.

Example B6

50 parts by weight of the cyanate ester of naphthol aralkyl obtained in Example A4 and 50 parts by weight of bis(4-maleimidephenyl)methane (BMI-H) were melt-blended at 160° C. for 10 minutes. Then, the melt-blended mixture was processed in the same manner as in Example B5 to obtain cured products. Table 5 shows the measurement results of the physical properties of the cured products.

Comparative Example B1

Cured products were obtained in the same manner as in Example B5 except that 70 parts by weight of the cyanate ester of naphthol aralkyl used in Example B5 was replaced with 70 parts by weight of bisphenol A dicyanate ester (CX, supplied by Mitsubishi Gas Chemical Company, Inc.). Table 5 shows the measurement results of the physical properties of the cured products.

Comparative Example B2

Cured products were obtained in the same manner as in Example B5 except that 50 parts by weight of the cyanate ester of naphthol aralkyl used in Example B6 was replaced with 50 parts by weight of bisphenol A dicyanate ester (CX). Table 5 shows the measurement results of the physical properties of the cured products.

TABLE 5

|  | Example B5 | Example B6 | Comparative Example B1 | Comparative Example B2 |
|---|---|---|---|---|
| Water absorption coefficient (%) | 2.9 | 3.7 | 8.9 | 10.0 |
| Appearance change after treatment | Nil | Nil | Present *) | Present *) |
| Bending strength (MPa) | 163 | 162 | 149 | 128 |
| Bend elastic constant (GPa) | 3.9 | 4.2 | 3.6 | 3.9 |
| Glass transition temperature (° C.) | 264 | 275 | 261 | 266 |

*) Cured product before treatment was transparent but the cured product became cloudy after the treatment.

(Measurement methods)
1) Water absorption coefficient and Appearance change after treatment:
A sample having a size of 30 mm×30 mm×3 mm was treated with a pressure cooker testing machine (PC-3 type, supplied by Hirayama Manufacturing Corporation) at 121° C. at 2 atmospheric pressure for 96 hours according to JIS C6481. Then, the sample was measured for a water absorption coefficient and an appearance change of the sample after water absorption was judged by visual observation.
2) Bending strength and Bend elastic constant:
A sample having a size of 10 mm×60 mm×4 mm was measured with an autograph (AG5000B, supplied by SHIMADZU CORPORATION) at normal temperature according to JIS-K6911.
3) Glass transition temperature:
A sample having a size of 5 mm×5 mm×3 mm was measured with a TMA device (TA Instrumen type 2940) at a loading of 5 g at a temperature-increasing rate of 10° C./min.

What is claimed is:

1. A cyanate ester compound represented by the formula (1),

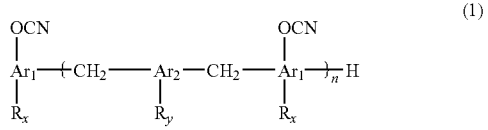

wherein
$Ar_2$ represents a phenylene group, a naphthylene group or a biphenylene group,
$Ar_1$ represents a naphthylene group or a biphenylene group when $Ar_2$ is a phenylene group, or $Ar_1$ represents a phenylene group, a naphthylene group or a biphenylene group when $Ar_2$ is a naphthylene group or a biphenylene group,
$R_x$ represents all substituents of $Ar_1$, each $R_x$ is the same or different and represents hydrogen, an alkyl group or an aryl group,
$R_y$ represents all substituents of $Ar_2$, each $R_y$ is the same or different and represents hydrogen, an alkyl group or an aryl group, and
n is an integer of 1 to 50.

2. A cyanate ester compound according to claim 1, wherein the compound of the formula (1) is a compound of the formula (2),

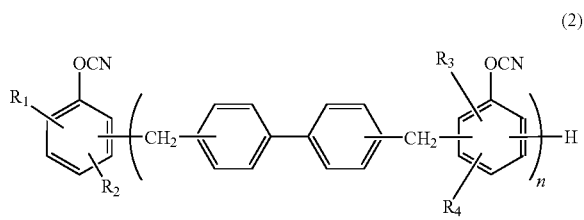

wherein $R_1$ to $R_4$ are the same or different and represent hydrogen or an alkyl group, n is an integer of 1 to 50, and the position of each substituent of aromatic rings can be arbitrarily selected.

3. A cyanate ester compound according to claim 1, wherein the compound of the formula (1) is a compound of the formula (3),

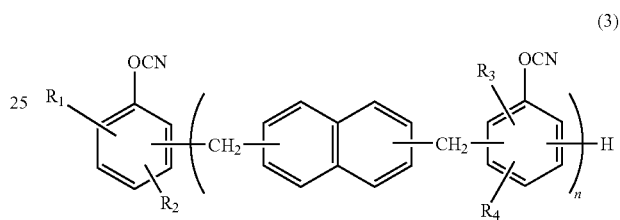

wherein $R_1$ to $R_4$ are the same or different and represent hydrogen or an alkyl group, n is an integer of 1 to 50, and the position of each substituent of aromatic rings can be arbitrarily selected.

4. A cyanate ester compound according to claim 1, wherein the compound of the formula (1) is a compound of the formula (4),

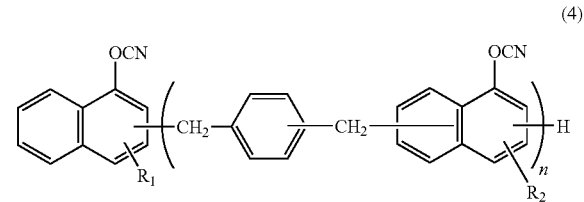

wherein $R_1$ and $R_2$ are the same or different and represent hydrogen or an alkyl group, n is an integer of 1 to 50, and the position of each substituent of aromatic rings can be arbitrarily selected.

5. A cyanate ester compound according to claim 2, wherein the compound of the formula (2) is a compound of the formula (5),

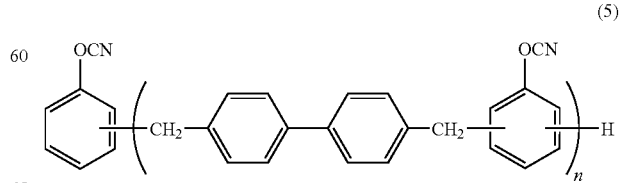

wherein n is an integer of 1 to 50.

6. A cyanate ester compound according to claim 3, wherein the compound of the formula (3) is a compound of the formula (6)

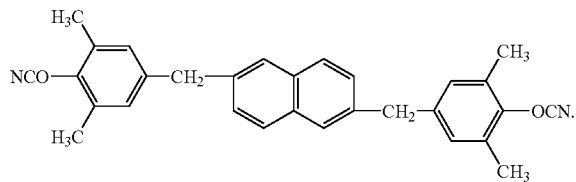
(6)

7. A cyanate ester compound according to claim 4, wherein the compound of the formula (4) is a compound of the formula (7),

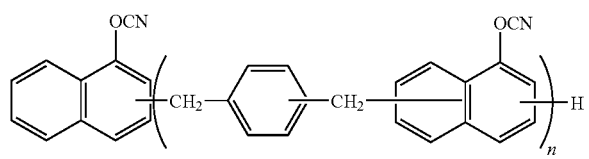
(7)

wherein n is an integer of 1 to 50.

8. A thermosetting resin composition containing the cyanate ester compound recited in claim 1 and a curing agent.

9. A cured product obtained by curing the thermosetting resin composition recited in claim 8.

10. A resin composition containing a cyanate ester compound of the formula (1) and an epoxy resin.

11. A resin composition according to claim 10, wherein the cyanate ester compound of the formula (1) is a cyanate ester compound represented by the formula (4) or the formula (7).

12. A resin composition according to claim 10, which further contains an inorganic filler.

13. A prepreg comprising the resin composition recited in claim 10 and a base material.

14. A laminate or a metal-foil-clad laminate obtained by curing the prepreg recited in claim 13.

15. A resin composition containing a cyanate ester compound of the formula (1) and a maleimide compound.

16. A resin composition according to claim 15, wherein the compound of the formula (1) is a cyanate ester compound represented by the formula (4) or the formula (7).

17. A cured product obtained by curing the resin composition recited in claim 15.

* * * * *